(12) United States Patent
Radwanski et al.

(10) Patent No.: US 9,974,899 B2
(45) Date of Patent: May 22, 2018

(54) METHOD FOR DELIVERING DESIRED LIGHT DOSE TO CELLS IN A LIGHT ATTENUATING MEDIUM

(71) Applicant: Fenwal, Inc., Lake Zurich, IL (US)

(72) Inventors: Katherine Radwanski, Des Plaines, IL (US); Min Kyungyoon, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 193 days.

(21) Appl. No.: 14/758,328

(22) PCT Filed: Feb. 6, 2013

(86) PCT No.: PCT/US2013/024893
§ 371 (c)(1),
(2) Date: Jun. 29, 2015

(87) PCT Pub. No.: WO2014/123521
PCT Pub. Date: Aug. 14, 2014

(65) Prior Publication Data
US 2015/0359959 A1  Dec. 17, 2015

(51) Int. Cl.
*A61M 1/36* (2006.01)

(52) U.S. Cl.
CPC ........ *A61M 1/3681* (2013.01); *A61M 1/3683* (2014.02); *A61M 1/3692* (2014.02); *A61M 1/3693* (2013.01); *A61M 1/3696* (2014.02); *A61M 2202/0407* (2013.01); *A61M 2202/0443* (2013.01); *A61M 2205/053* (2013.01); *A61M 2205/33* (2013.01)

(58) Field of Classification Search
CPC .............. A61M 1/3681; A61M 1/3683; A61M 1/3692; A61M 1/3693; A61M 1/3696; A61M 2205/0407; A61M 2205/0443; A61M 2205/053; A61M 2205/33
See application file for complete search history.

(56) References Cited

U.S. PATENT DOCUMENTS 6,219,584 B1 * 4/2001 Lee ..................... A61M 1/3681
436/519
6,277,337 B1    8/2001 Goodrich, Jr. et al.
(Continued)

FOREIGN PATENT DOCUMENTS

DE    4235841 A1    4/1994
EP    1674120 A1    6/2006
WO    97/36581 A1   10/1997

*Primary Examiner* — Benjamin Klein
(74) *Attorney, Agent, or Firm* — Cook Alex Ltd.

(57) ABSTRACT

A method provided for determining a range for the amount of light-energy attenuating material that may be present in a suspension containing target cells (such as MNCs), light-energy attenuating matter (such as RBCs and plasma), and a light-energy activatable compound (such as psoralen) so that a desired therapeutic effect (such as the percentage of MNCs in which apoptosis occurs) is obtained when the suspension is subjected to a known amount of light energy. In a related aspect, a method is provided for preparing a suspension containing target cells, light-energy attenuating matter, and a light-energy activatable compound so that a desired therapeutic effect is obtained when the suspension is subjected to a known amount of light energy.

10 Claims, 7 Drawing Sheets

(56) References Cited

U.S. PATENT DOCUMENTS

2005/0049539 A1\* 3/2005 O'Hara, Jr. ......... A61M 1/3681
  604/4.01
2005/0163778 A1\* 7/2005 Peritt ..................... A61K 35/15
  424/145.1

\* cited by examiner

METHOD FOR DELIVERING DESIRED LIGHT DOSE TO CELLS IN A LIGHT ATTENUATING MEDIUM

FIELD OF THE DISCLOSURE

The present disclosure is directed to a method for delivering a desired or target light dose to cells which are suspended in a light attenuating medium, and, more particularly to a method that delivers a target light dose for a fixed emitted light dose, even if there is some variation in the amount of light attenuating medium in the suspension.

Light irradiation therapy is used for the treatment of various blood diseases to, e.g., eliminate immunogenicity in cells, inactivate or kill selected cells, inactivate viruses or bacteria, or activate desirable immune responses. For example, it is known to use the photoactivatable drug psoralen to treat pathogenic blood cells, such as lymphocytes, in an extracorporeal photopherisis (ECP) procedure in which the patient receives 8-methoxypsoralen (8-MOP), blood is withdrawn from the patient, the white cells separated (typically by centrifugation), and subjected to UV light to activate the 8-MOP molecules. The photoactivated 8-MOP alters the DNA of the pathogenic leukocytes, and the fluid with the altered leukocytes is reinfused back into the patient to induce an immune system response.

A difficulty in performing phototherapy is the delivery of the proper dose of light energy to the photoactivatable material in the suspension, particularly if the suspension includes material that is not substantially transparent to light so that it attenuates the light energy intended for photoactivation, or if the target cells are not uniformly distributed on the fluid surface, in which case target cells closest to the surface may serve to attenuate light energy with respect to those target cells beneath the surface.

A method for delivering a desired dose of light energy to a suspension is disclosed in U.S. Pat. No. 6,219,584, to Therakos, Inc. This patent is directed to an "online" photopheresis system that includes both the blood separation device and the photoactivation device in an integrated, closed system. In the Therakos system, a complex algorithm is used to determine the emitted dose ("fluid light energy value" or FLEV) needed to achieve the target dose (the "target's effective light energy value" or TELEV) that is to be delivered to the targeted leukocytes (mononuclear cells or MNC). This algorithm requires knowledge of the thickness ratio of the product, as well as the light transmittance value of the product is measured for every product using a hematocrit sensor.

In "offline" methods, (such as those practiced when using the phototherapy systems available from Macopharma SA or Vilber Lourmet), the UV dose is monitored by sensors which are angled to detect UV light emitted from the UV bulbs as well as that reflected from the mirrored surface behind each set of bulbs (and presumably less light is reflected back if the treated cell product is absorbing more light). This method does not fully account for the UV light being absorbed by the red cells and plasma, and operators are required to manually measure the product hematocrit and adjust it (if necessary) to lower than 2% because the UV dose delivered at higher hematocrits is unknown (and likely insufficient).

In accordance with the method described below, a hematocrit sensor is not required, but only moderate control of a preset product volume and hematocrit of the suspension to be treated is required. The desired light dose to be received by the target cells is determined based on the therapeutic response of the target cells, thus providing for a more precise therapeutic result than simply applying a correction factor to the emitted light dose.

SUMMARY OF THE DISCLOSURE

In a first aspect of the disclosure, a photopheresis system is provided comprising a disposable fluid circuit having a processing chamber for separating whole blood into one or more components including mononuclear cells and at least one treatment container for receipt of separated mononuclear cells having a predetermined thickness when a known volume of suspended mononuclear cells is received therein; a separation device adapted to receive the processing chamber for effecting separation of mononuclear cells from whole blood, an irradiation device adapted to receive the storage container, and a controller configured to control the hematocrit of the suspended mononuclear cells received in the storage container.

Preferably, the treatment container has a predetermined thickness of from approximately 4 mm to 5 mm when it contains the known volume of suspended mononuclear cells, and more preferably a thickness of 4.5 mm, while the controller provides suspended mononuclear cells having a hematocrit of from 2%-3%, and more preferably a hematocrit of 2.5%.

In a second aspect of the disclosure, a method for performing a photopheresis procedure is provided. The method comprises providing a disposable fluid circuit comprising a processing chamber for separating whole blood into one or more components including mononuclear cells and at least one treatment container adapted to receive mononuclear cells, and separating from a source of whole blood a mononuclear cell product on an apheresis device adapted to receive the processing chamber. The method further comprises combining the cell product with an activation agent and introducing the suspension of the combined separated cell product and activation agent into the treatment chamber such that the suspension has a predetermined hematocrit and a predetermined thickness. The cell product suspension is then exposed to light in an irradiation device to obtain a treated cell product. The treated cell product is then returned to the source.

Preferably, the treatment container provides for a predetermined thickness for the suspended mononuclear cells of from approximately 4 mm to 5 mm, and more preferably a thickness of 4.5 mm, while the suspended mononuclear cells have a hematocrit of from 2%-3%, and more preferably a hematocrit of 2.5%.

In a further aspect of the disclosure, a method is provided for determining a range for the amount of light-energy attenuating material that may be present in a suspension containing target cells, light-energy attenuating matter, and a light-energy activatable compound so that a desired therapeutic effect is obtained when the suspension is subjected to a known amount of light energy.

In this aspect, a plurality of first samples is prepared that contains target cells, light-energy activatable compound, and containing substantially no light-energy attenuating matter. Then, known amounts of light energy are applied to each first sample. The therapeutic response of each of the first samples is measured and then compared to the amount of light applied thereto, thus permitting prediction of the amount of light-energy delivered to a suspension containing target cells based on the therapeutic response.

Then a plurality of second samples is prepared containing target cells, varying amounts of light-energy attenuating matter, and light-energy activatable compound. Known amounts of light energy are then applied to each second sample and the therapeutic response of each second sample is measured. The therapeutic response of each second sample is then compared to the therapeutic responses of the first samples to determine the amount of light energy absorbed by each second sample to obtain the therapeutic response.

Then, the ratio of light energy absorbed by each second sample to the amount of light energy applied to each second sample based on the therapeutic responses of the second samples is determined, and the ratio for each second sample is compared against the varying amounts of light-energy attenuating matter in each second sample so as to determine a range of varying amounts of light-energy attenuating matter for which the ratio is such that the slope of the plot is substantially flat.

In a preferred method and more specific example of the first aspect, the target cells are Mononuclear Cells (MNCs), the light energy attenuating matter is red blood cells and plasma, the light-energy activatable compound is psoralen, and the desired therapeutic effect is the percentage of cells in which apoptosis occurs. Further, the amount of light attenuating matter in the second samples may be varied by varying the hematocrit HCT and the volume or thickness of each second sample.

In a related aspect of the present disclosure, a method is provided for preparing a suspension containing target cells, light-energy attenuating matter, and a light-energy activatable compound so that a desired therapeutic effect is obtained when the suspension is subjected to a known amount of light energy. The range for the amount of light-energy attenuating material that may be present in a suspension so that a desired therapeutic effect is obtained when the suspension is subjected to a known amount of light energy is determined as set forth above. Then, the suspension to be treated is prepared such that the amount of light-attenuating matter is within the range.

Other aspects of the disclosure will become apparent upon references to the accompanying figures and following detailed description.

DESCRIPTION OF THE ILLUSTRATED EMBODIMENTS

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
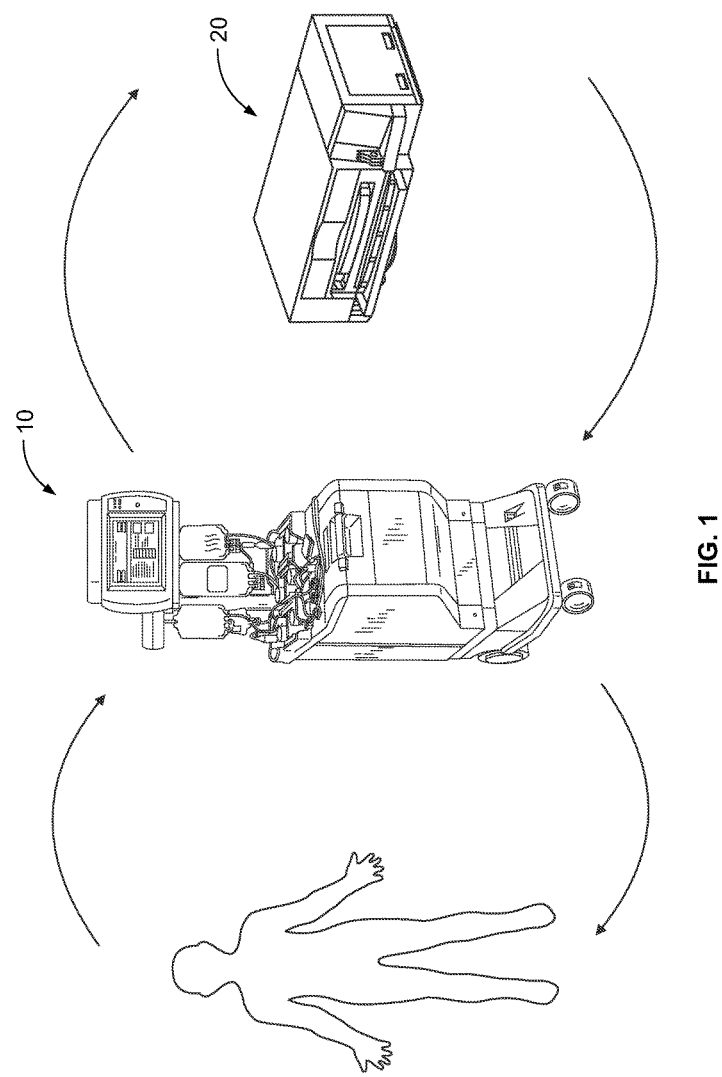
FIG. 1 is a diagram generally showing the mechanical components of an exemplary photopheresis treatment as described herein.

FIG. 1 shows, in general, the mechanical components that make up the system and that are used in the methods described herein. In accordance with the present disclosure, the system includes a separation component 10 and a treatment (i.e., irradiation) component 20. Preferably, irradiation component 20 is independent and housed separately from separation component 10. Although separately housed and independent devices, it is preferable that separation device 10 and irradiation device 20 are located adjacent to each other. While FIG. 1 shows a preferred embodiment of separated separation and irradiation components, it will be appreciated that the methods described herein may also be used with devices having integrated separation and irradiation components, such as the Therakos system described above.

Figure 4:
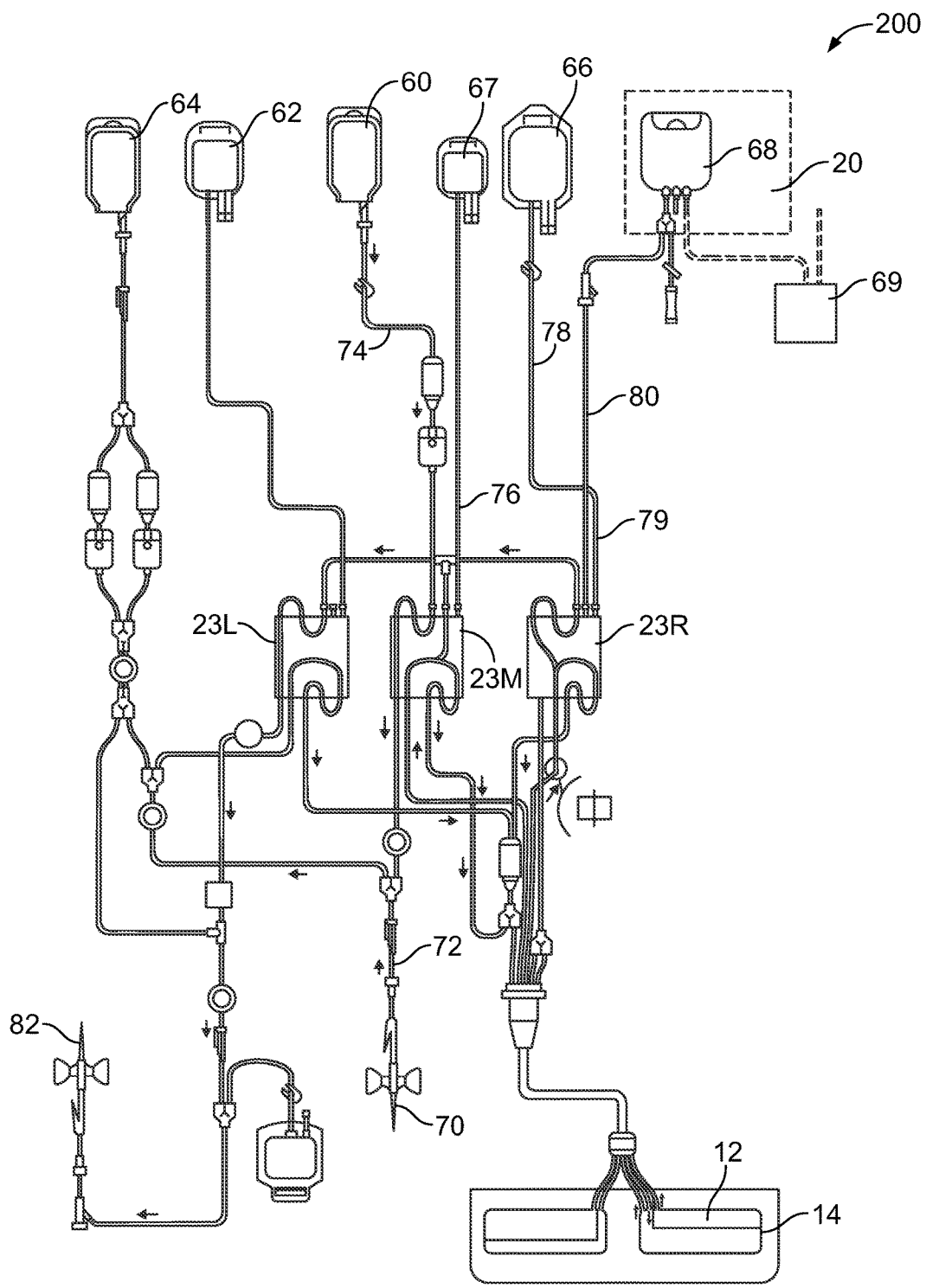
FIG. 4 is a diagram of the fluid circuit useful in the collection, treatment and reinfusion of mononuclear cells as described herein.

In accordance with the systems and methods described herein a patient is connected to a blood processing set, i.e., fluid circuit 200. As generally illustrated in FIGS. 1 and 4, fluid circuit 200 provides a sterile closed pathway between separation component 10 and irradiation component 20. The system described herein also optionally includes a washing component which, preferably, is housed within the separation component. Preferably, the separation component 10 and washing component are one and the same.

With reference to FIG. 1, whole blood is withdrawn from the patient and introduced into the separation component 10 where the whole blood is separated to provide a target cell population. In a preferred embodiment in accordance with the present disclosure, the target cell population may be mononuclear cells. Other components separated from the whole blood, such as red blood cells and platelets may be returned to the patient or collected in pre-attached containers of the blood processing set.

The separated target cell population, e.g., mononuclear cells, is then prepared for treatment and irradiation in treatment component 20. As discussed above, in accordance with the present disclosure, treatment of mononuclear cells involves the photoactivation of a photoactive agent that has been combined with the mononuclear cells. Once treated, the mononuclear cells may optionally be provided to a washing component, which, as shown in FIG. 1, is housed within separation component 10. The treated mononuclear cells are separated from the supernatant and the concentrated cells may be returned to the patient. The supernatant liquid will typically include excess and unbound photoactivation agent. Optionally, the concentrated cells may further be combined with a suitable wash solution within separation/washing component 10. If washing of the treated mononuclear cells is performed, the suspension of mononuclear cells in a wash solution is then subjected to a centrifugal field (or other environment which can effect separation of the fluid components), whereby the mononuclear cells are concentrated and separated from the supernatant, including any remaining unbound photoactivation agent. Supernatant may then be diverted to an appropriate waste container, while the treated mononuclear cells are returned to the patient, as generally shown in FIG. 1.

Figure 2:
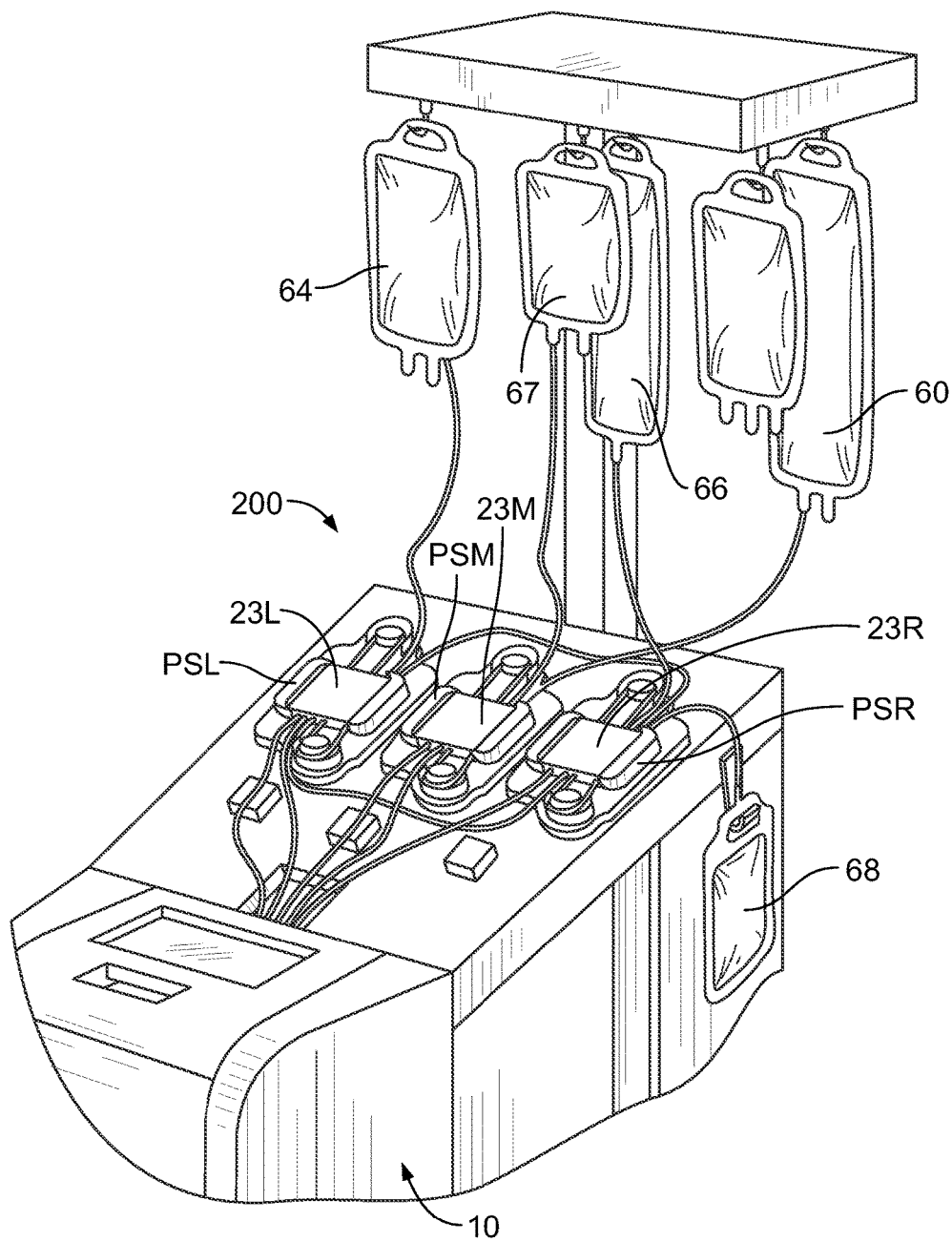
FIG. 2 is a partial perspective view of a multifunctional apheresis separator useful in the methods and systems described herein.
Figure 3:
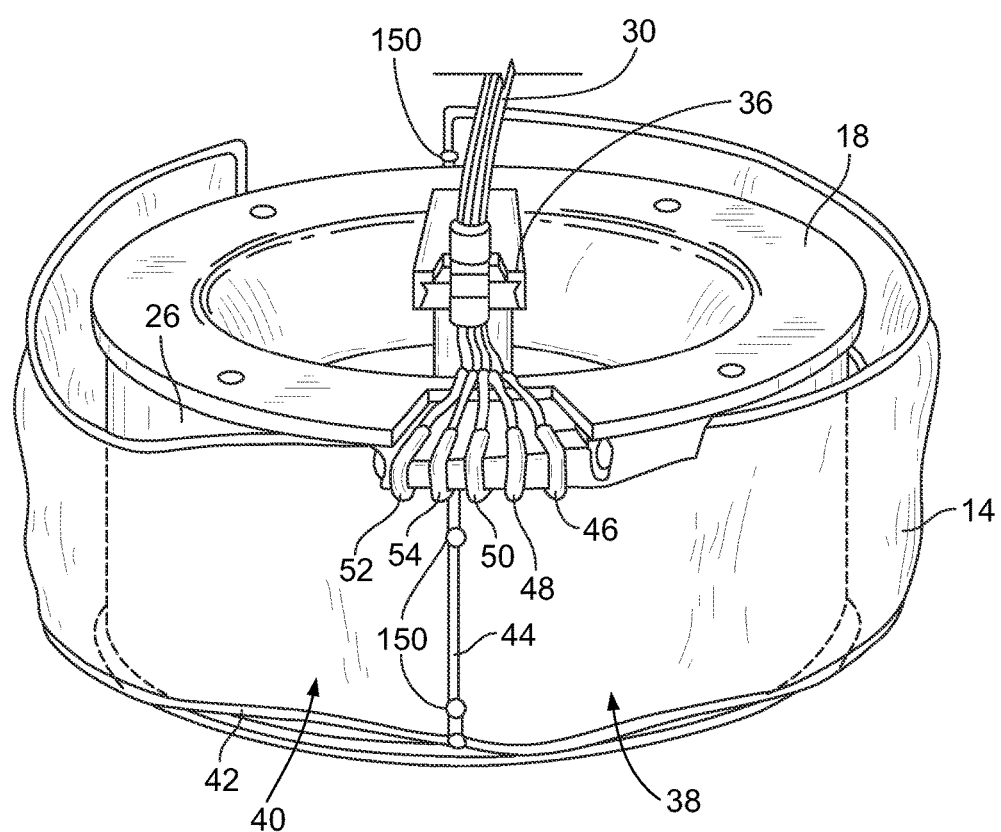
FIG. 3 is a perspective view of a processing container (separation chamber) of the processing set used with the separator of FIG. 2.

Apparatus useful in the collection (and washing) of mononuclear cells, and providing the separation component 10 of FIG. 1, include the Amicus® Separator made and sold by Fenwal, Inc., of Lake Zurich, Ill. Mononuclear cell collections using a device such as the Amicus® are described in greater detail in U.S. Pat. No. 6,027,657, the contents of which is incorporated by reference herein in its entirety. Briefly, FIGS. 2-4 show a representative blood centrifuge 10 with fluid circuit 200 mounted thereon (FIG. 2), the fluid circuit (FIG. 4) having a blood processing container 14 (see FIG. 3) defining a separation chamber suitable for harvesting mononuclear cells (MNC) from whole blood. As shown in FIG. 2, a disposable processing set or fluid circuit 200 (which includes container 14) is mounted on the front panel of centrifuge 10. The processing set (fluid circuit 200) includes a plurality of processing fluid flow cassettes 23L, 23M and 23R with tubing loops for association with peristaltic pumps on device 10. Fluid circuit 200 also includes a network of tubing and pre-connected containers for establishing flow communication with the patient and for processing and collecting fluids and blood and blood components, as shown in greater detail in FIG. 4.

As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and is preferably pre-attached to with the disposable set 200. Alternatively, container 68 may be attached to set 200 by known sterile connection techniques, such as sterile docking or the like. With reference to FIG. 4, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. The blood processing set includes one or more venipuncture needle(s) for accessing the circulatory system of the patient. As shown in FIG. 4, fluid circuit 200 includes inlet needle 70 and return needle 82. In an alternative embodiment, a single needle can serve as both the inlet and outlet needle.

Fluid flow through fluid circuit 200 is preferably driven, controlled and adjusted by a microprocessor-based controller in cooperation with the valves, pumps, weight scales and sensors of device 10 and fluid circuit 200, the details of which are described in the previously mentioned U.S. Pat. No. 6,027,657.

The fluid circuit is further adapted for association with the treatment component (i.e., irradiation device) 20. Apparatus for the irradiation of the mononuclear cells are also known and are available from sources such as Cerus Corporation, of Concord, Calif. One example of a suitable irradiation device is described in U.S. Pat. No. 7,433,030, the contents of which is likewise incorporated by reference herein in its entirety. As shown and described in U.S. Pat. No. 7,433,030, irradiation device preferably includes a tray or other holder for receiving one or more containers during treatment. Other irradiation devices may also be suitable for use with the method and system described herein, including devices available from Macopharma and/or Vilber Lourmet.

As noted above, separation chamber 12 is defined by the walls of a flexible processing container 14 carried within an annular gap defined by a rotating spool element 18 and an outer bowl element (not shown). The processing container 14 takes the form of an elongated tube which is wrapped about the spool element 18 before use. The bowl and spool element 18 are pivoted on a yoke between an upright position and a suspended position, also not shown. In operation, the centrifuge 10 rotates the suspended bowl and spool element 18 about an axis 28, creating a centrifugal field within the processing chamber of container 14. Details of the mechanism for causing relative movement of the spool 18 and bowl elements as just described are disclosed in U.S. Pat. No. 5,360,542 entitled "Centrifuge with Separable Bowl and Spool Elements Providing Access to the Separation Chamber," which is also incorporated herein by reference.

Figure 5:
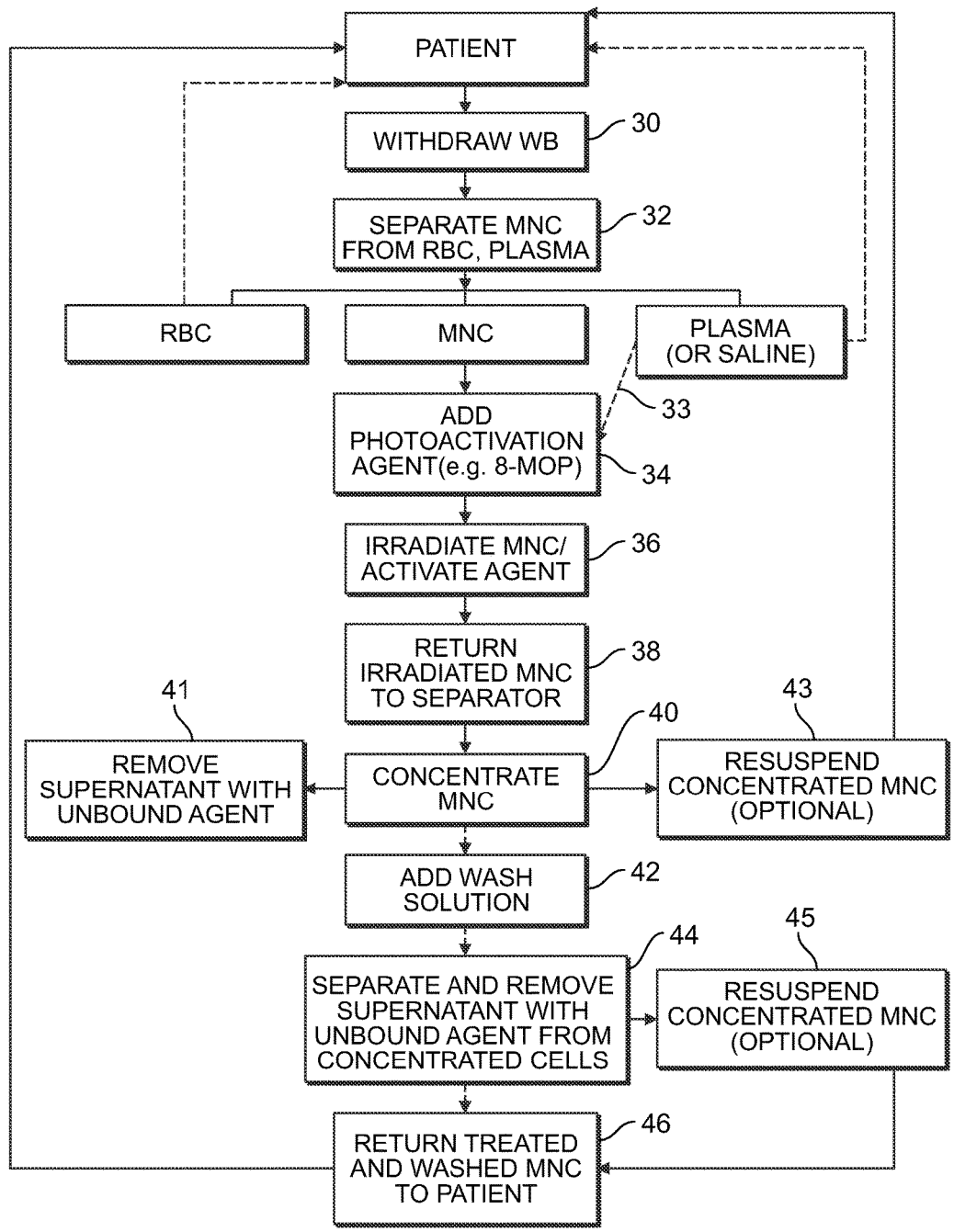
FIG. 5 is a flow chart setting forth the steps of the method of a photopheresis treatment as described herein.

With reference to FIG. 5, a representative method of treating mononuclear cells is seen. First, whole blood is withdrawn from a patient (step 30) through inlet needle 70 and introduced into the separation chamber 12 of container 14 of processing set 200, where the whole blood is subjected to a centrifugal field. The centrifugal field separates the target cell population, i.e., mononuclear cells, from red blood cells, platelets and plasma (step 32). The components such as red blood cells and platelets may be returned to the patient or may be diverted to a container (e.g., container 67) for further processing. Collection of the mononuclear cells may proceed in one or more cycles, with the number of processing cycles conducted in a given therapeutic procedure depending upon the total volume of MNC to be collected.

Effective treatment of the mononuclear cells with light may require that the collected mononuclear cells are provided in a suspension having a suitable hematocrit. Specifically, and as discussed in greater detail below, the level of hematocrit of the MNC suspension to be treated affects the amount of UV light absorbed by the MNC, as the red blood cells in the MNC suspension will block at least a portion the UV light from reaching the targeted MNCs. Precise control of hematocrit may be difficult to achieve, particularly with systems in which hematocrit sensors are used for this purpose. If the hematocrit of the suspended MNCs is too high (such that the red blood cells will interfere with the absorption of light by the MNCs), it may be desired or even necessary to dilute the mononuclear cells with a diluting solution, such as plasma or saline, as shown in step 33, to control the hematocrit so that a desired amount of UV light will reach the targeted MNC. The diluted mononuclear cells (in container 68) are then combined with the suitable photoactivation agent in step 34. Alternatively, the desired volume of the agent may be pre-added to the container.

As noted above, the mononuclear cells collected in accordance with the mononuclear cell collection process described above may be collected in container 68 that is suitable for irradiation by light of a selected wavelength. By "suitable for irradiation" it is meant that the walls of the container are sufficiently transparent to light of the selected wavelength to activate the photoactive agent. In treatments using UVA light, for example, container walls made of ethylene vinyl acetate (EVA) are suitable. Accordingly, container 68 in which the mononuclear cells are collected may serve both as the collection container and the irradiation container. Container 68 may be placed inside irradiation device 20 by the operator or, more preferably, may be placed inside the irradiation chamber of irradiation device 20 at the beginning of the ECP procedure and prior to whole blood withdrawal (as shown by the broken lines representing device 20 in FIG. 4). In any event, container 68 preferably remains integrally connected to the remainder of fluid circuit 200 during the entire procedure, thereby maintaining the closed or functionally closed condition of fluid circuit 200.

Automated control of the MNC collection and the irradiation treatment may be effected by the microprocessor-based controller of the respective separation device 10 and irradiation device 20 with some operator input for each device. Alternatively, operation of both separation device 10 and irradiation device 20 and the process steps carried out by each may be remotely controlled by a separate controller (e.g., a computer) that communicates with both.

The mononuclear cells with photoactivation agent (8-MOP) are then irradiated for a selected period of time (step 36). In one non-limiting example, during treatment, the mononuclear cell product may be exposed to UV bulbs having a wavelength in the UVA range of about 320 nm to 400 nm for a selected period of time, such as approximately 10-60 minutes, resulting in an average UVA exposure of approximately 0.5-5.0 $J/cm^2$ and use preferably approximately 1-2 $J/cm^2$ or even more preferably approximately 1.5 $J/cm^2$ per lymphocyte.

Once treatment is complete, the treated mononuclear cells may be returned to separator 10 (and more specifically, the separation chamber 12 of container 14) as shown in step 38 of FIG. 5. Once inside chamber 12, the MNC may be concentrated (step 40) to allow for the concentrated cells to have a smaller total volume as compared to un-concentrated cells. As a result, a smaller volume of concentrated MNCs may be reinfused to a patient faster. The concentrated cells may be resuspended in a suitable resuspension medium (e.g., plasma, saline) as shown in step 43 and returned to the patient. Optionally, prior to return to the patient, the concentrated and treated cells may be combined with a suitable wash solution (step 42), supplied (by the pumping action of pumps associated with cassette 23R) from containers 66 and/or 64 (see FIG. 4) is added to the concentrated cells.

In a method according to the present disclosure, a target light dose is determined by generating a standard curve relating light dose delivered to desired result. More specifically, a light attenuation curve is generated relating concentration of the light attenuating material to percent light absorbed by the attenuating material. The parameters of the product intended for treatment are targeted to a substantially flat portion of the light attenuation curve (i.e., where the percentage of light absorbed is not as sensitive to the product parameters). As a result, a selected fixed light dose is emitted which will deliver approximately the target light dose even with variations in the product parameters, meaning that precise control of the parameter is not required.

As one example, in photopheresis therapy, target cells such as mononuclear cells (MNCs) are combined with a psoralen (such as 8-MOP) and irradiated with UV light (specifically UV-A light). The UV light crosslinks 8-MOP to DNA strands inside the cell and on the cell wall, eventually causing apoptosis of the treated cells. As part of the collection procedure, the MNC product treated during photopheresis contains some amount of red blood cells and plasma, both of which absorb UV light, thereby preventing some portion of the UV light from being delivered to the desired target cells (e.g., MNC). As a result, the UV dose emitted from the UV source(s) is not equal to the UV dose delivered to the MNC.

To address this, a standard curve (delivered UV dose vs. lymphocyte apoptosis) can be generated by applying known UV doses to MNCs in the absence of RBC and plasma (which comprise the light attenuating material), and monitoring the apoptotic response in the lymphocytes after certain time points in culture, as discussed further below in connection with FIG. 1.

A second standard curve can be generated relating the hematocrit (which corresponds to the concentration of light attenuating material) to the percentage of light absorbed ($=(1-(delivered/emitted))\times100\%$), as discussed below in connection with FIG. 2. From this curve, the product parameters for the procedure can been chosen from an area of the curve that is substantially flat (i.e., has a low slope) such that the parameters of the product (hematocrit and volume, the latter corresponding to the product thickness) can vary slightly without significant impact on the UV light dose delivered to the MNC. The light dose vs. desired result curve can be generated at varying 8-MOP concentrations and/or at multiple time points in culture (24, 48, 72 hours).

EXAMPLE

A. Correlating Delivered Light Dose to Therapeutic Response

The creation of a standard curve relating light dose (UVA in this case) delivered to an apoptotic response in the lymphocytes (desired result) for a suspension containing essentially no light attenuating material was determined as set forth below.

Figure 6:
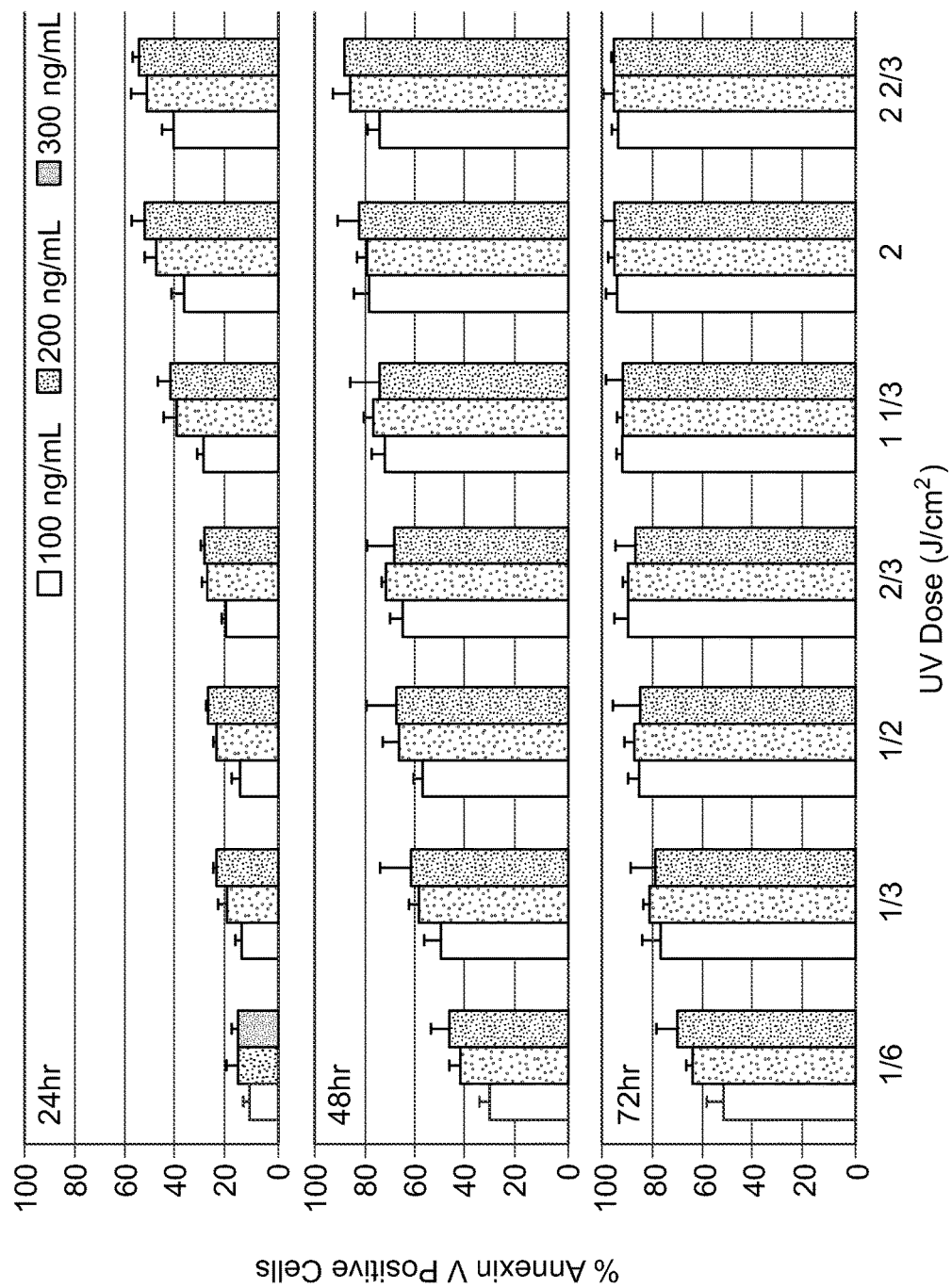
FIG. 6 is a series of three bar charts showing the degree of therapeutic response (the % of Annexin V Positive Cells) for varying light energy doses (in $J/cm^2$) and different amounts of light activatable compound (8-MOP at 100 ng/mL, 200 ng/mL and 300 ng/mL) at 24 hours, 48 hours and 72 hours.

Apheresis-derived mononuclear cells from healthy donors were processed using a Ficoll-Paque gradient to produce a purified MNC population. The MNCs were then resuspended at $5\times10^6$ or $50\times10^6$ leukocytes/mL in RPMI 1640 media with 2 mM glutamine. The MNCs were transferred to 60 mm polystyrene culture dishes (5 mL cells/dish) and incubated with 100, 200 or 1300 ng/mL of 8-MOP for 15 minutes in the dark. Irradiation was performed using an LED array capable of light intensities of $11.6\pm0.2$ $mW/cm^2$ in the UVA band at $365\pm10$ nm. After irradiation, MNCs were washed with RPMI 1640 media and resuspended at $1-2\times10^6$/mL in RPMI 1640 media with 2 mM glutamine and 10% human serum. Cells were cultured at 37° C. in a humidified chamber with 5% $CO_2$ for up to 72 hours. After 24, 48 and 72 hours, samples were assayed for apoptosis. Lymphocyte apoptosis was measured as the percentage of CD45+/Annexin-V positive cells in the lymphocyte forward/side scatter gate. Samples were repeated for at least n=3 at each UV dose/8-MOP concentration. Bar charts relating the percentage of Annexin-V positive cells at 24, 48 and 72 hours for various UV doses are seen in FIG. 6.

B. Correlating Light Dose Absorbed to Amount of Attenuating Material

Then, a standard curve was generated relating hematocrit (i.e., the concentration of light attenuating material) and thickness of the product to the percentage of UV light absorbed was determined as set forth below.

Figure 7:
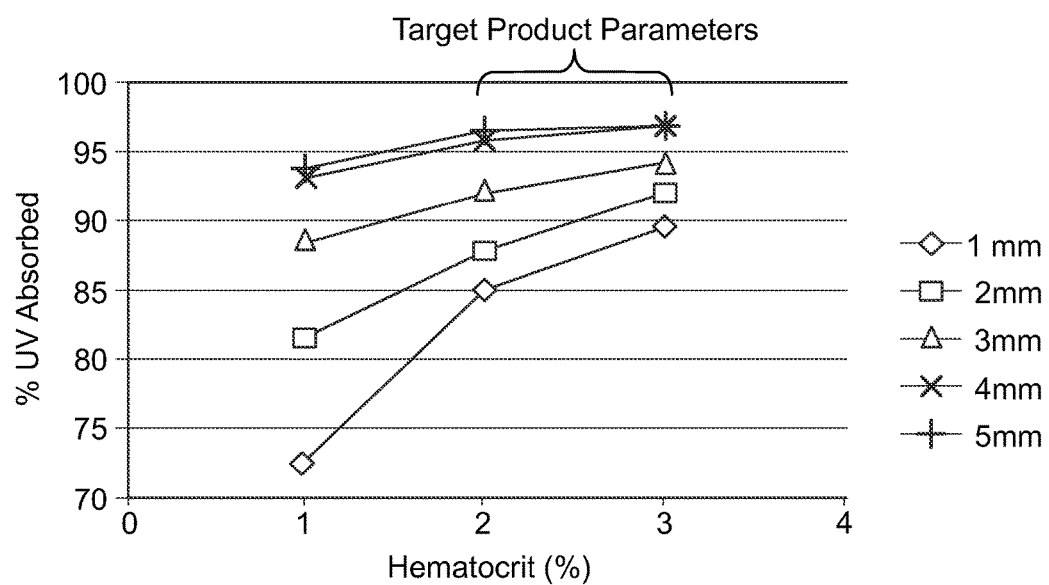
FIG. 7 is a plot of the % of light energy (UV) absorbed by a sample vs. the amount of light attenuating matter in the sample (% HCT) for various sample thicknesses (1 mm, 2 mm, 3 mm, 4 mm, and 5 mm).

Apheresis-derived mononuclear cells (MNCs) from healthy donors were processed using a Ficoll-Paque gradient to produce a purified MNC population. Cells were resuspended at $10\times10^6$ leukocytes/mL in RPMI 1640 media with 2 mM glutamine. Red blood cells (the light attenuating material) were added to achieve 1, 2 or 3% hematocrit followed by incubation with 200 ng/mL of 8-MOP for 15 minutes in the dark. Cells were transferred to 60 mm polystyrene culture dishes at 2.83, 5.65, and 8.48 mL cells/dish to achieve product thicknesses of 1 mm, 2 mm, 3 mm, 4 mm (the sum of 1 mm plus 3 mm), and 5 mm (the sum of 2 mm plus 3 mm). Irradiation was performed using a commercially available UVA light box (Cerus). After irradiation, cells were again processed using a Ficoll-Paque gradient to produce purified MNCs. Final wash was performed with RPMI 1640 media and cells were resuspended at 1-2×10$^6$/mL in RPMI 1640 media with 2 mM glutamine and 10% human serum. Cells were cultured at 37° C. in a humidified chamber with 5% $CO_2$ for up to 72 hours. After 24, 48 and 72 hours, samples were assayed for apoptosis. Lymphocyte apoptosis was measured as the percentage of CD45+/Annexin-V positive cells in the lymphocyte forward/side scatter gate. Samples were repeated for at least n=3 at each hematocrit/thickness combination. UV dose delivered in each sample was determined from reading the bar charts of FIG. 1 based on apoptotic response. The percentage of UV absorbed was calculated as $$= \left(1 - \frac{UV_{delivered}}{UV_{emitted}}\right) \times 100\%$$

and this percentage was plotted against the hematocrit of the samples at the various product thicknesses to generate a graph as seen in FIG. 7.

With reference to FIG. 7, the plots for the samples having a thickness of 4 mm and 5 mm is substantially flat for suspensions having a HCT of from 2 to 3. Thus, target product parameters according to the present method would be to prepare a suspension having approximately 2.5% HCT with a thickness of approximately 4.5 mm, while appreciating that the actual product hematocrit could vary from 2-3%, and the thickness could vary from 4-5 mm, without a significant impact on the UV dose delivered to the MNC, thereby still achieving the desired result. In practice, the hematocrit for the MNC suspension is preferably designed into the apheresis procedure by which the MNC is collected, while the thickness of the suspension to be treated is controlled by knowing the surface area of the UV treatment container and the volume of the MNC suspension pumped into the container.

Thus, systems and methods have been disclosed for preparing a suspension to be subjected to light energy that includes light attenuating matter such that a desired dose is received and the desired therapeutic effect obtained. While the method has been described in the context of the extracorporeal photopheresis of mononuclear cells, it is not limited to the same, as other light dose cell treatment protocols could also utilize this method (i.e., pathogen inactivation).

The invention claimed is:

1. A photopheresis system comprising:
 a disposable fluid circuit having a processing chamber for separating whole blood into a cell product comprising a suspension of mononuclear cells and red blood cells, and at least one treatment container for receipt of the suspension of mononuclear cells and red blood cells, the treatment container having a predetermined thickness of from approximately 4 mm to 5 mm when a known volume of the suspension of mononuclear cells and red blood cells is received therein;
 a separation device adapted to receive the processing chamber for effecting separation of mononuclear cells and red blood cells from whole blood;
 an irradiation device adapted to receive the treatment container, and to subject the treatment container to a selected fixed emitted light dose; and
 a controller configured to control the separation device so that the suspension of mononuclear cells and red blood cells received in the treatment container has a hematocrit within a predetermined range of from 2%-3% prior to irradiation and to control the irradiation device to deliver the selected fixed emitted light dose regardless of the hematocrit of the suspension of mononuclear cells and red blood cells.

2. The photopheresis system of claim 1 wherein the treatment container has a thickness of 4.5 mm.

3. The photopheresis system of claim 2 wherein the controller is configured to provide the suspension of mononuclear cells and red blood cells a hematocrit of 2.5% prior to irradiation.

4. The system of claim 1 wherein the selected fixed emitted light dose is determined by generating a light attenuation curve relating hematocrit of the suspension of mononuclear cells and red blood cells to percent light absorbed by the red blood cells for a predetermined thickness of the treatment container when a known volume of the suspension of mononuclear cells and red blood cells is received therein, and targeting the selected fixed emitted light dose to a flat portion of the light attenuation curve.

5. A method for performing an extracorporeal photopheresis procedure comprising the steps of:
 a) obtaining a disposable fluid circuit comprising a separation chamber for separating a biological fluid comprising mononuclear cells and red blood cells into a cell product comprising mononuclear cells and red blood cells, and at least one treatment container adapted to receive said cell product, said circuit providing a sterile closed pathway between the separation chamber and the treatment container,
 b) mounting said separation chamber onto an apheresis device and mounting said treatment container onto an irradiation device, said apheresis device including at least one pump for effecting fluid flow through said circuit,
 c) introducing from a source of biological fluid a volume of said biological fluid into said separation chamber and separating said cell product comprising mononuclear cells and red blood cells from said volume of biological fluid inside said separation chamber,
 d) combining said separated cell product comprising mononuclear cells and red blood cells with a selected amount of an activation agent to form a suspension having a hematocrit within a pre-determined range of from 2% to 3%,
 e) introducing said suspension of separated cell product comprising mononuclear cells and red blood cells and activation agent into said treatment container by action of said at least one pump of said apheresis device such that the suspension has a predetermined thickness of from 4 mm to 5 mm;
 f) treating said suspension of mononuclear cells, red blood cells and activation agent with a selected fixed emitted light dose regardless of the hematocrit of the suspension in said irradiation device; and
 g) withdrawing said treated suspension from said treatment chamber by the action of said at least one pump of said apheresis device.

6. The method of claim 5 wherein the hematocrit of the suspension is 2.5% and the thickness of the suspension within the treatment container is 4.5 mm.

7. The method of claim 5 wherein the thickness of the suspension in the treatment chamber is determined by providing a treatment container having a known surface area and operating the at least one pump of the apheresis device to introduce a known volume of the suspension of combined separated cell product and activation agent.

8. A method for performing an extracorporeal photopheresis procedure comprising the steps of:
   a) obtaining a disposable fluid circuit comprising a separation chamber for separating a biological fluid comprising mononuclear cells and red blood cells into a cell product comprising mononuclear cells and red blood cells, and at least one treatment container adapted to receive said cell product, said circuit providing a sterile closed pathway between the separation chamber and the treatment container,
   b) mounting said separation chamber onto an apheresis device and mounting said treatment container onto an irradiation device, said apheresis device including at least one pump for effecting fluid flow through said circuit,
   c) introducing from a source of biological fluid a volume of said biological fluid into said separation chamber and separating said cell product comprising mononuclear cells and red blood cells from said volume of biological fluid inside said separation chamber,
   d) combining said separated cell product comprising mononuclear cells and red blood cells with a selected amount of an activation agent to form a suspension having a hematocrit within a pre-determined range,
   e) introducing said suspension of separated cell product comprising mononuclear cells and red blood cells and activation agent into said treatment container by action of said at least one pump of said apheresis device such that the suspension has a predetermined thickness;
   f) treating said suspension of mononuclear cells, red blood cells and activation agent with a selected fixed emitted light dose regardless of the hematocrit of the suspension in said irradiation device; and
   g) withdrawing said treated suspension from said treatment chamber by the action of said at least one pump of said apheresis device;
   wherein the selected fixed emitted light dose is determined by generating a light attenuation curve relating hematocrit of the suspension of mononuclear cells, red blood cells and activation agent to percent light absorbed by the red blood cells for a predetermined thickness of the treatment container when a known volume of the suspension is received therein, and targeting the selected fixed emitted light dose to a flat portion of the light attenuation curve.

9. The method of claim 8 wherein the thickness of the suspension in the treatment chamber is determined by providing a treatment container having a known surface area and operating the at least one pump of the apheresis device to introduce a known volume of the suspension of combined separated cell product and activation agent.

10. A photopheresis system comprising:
   a disposable fluid circuit having a processing chamber for separating whole blood into a cell product comprising a suspension of mononuclear cells and red blood cells, and at least one treatment container having a thickness of 4.5 mm for receipt of the suspension of mononuclear cells and red blood cells;
   a separation device adapted to receive the processing chamber for effecting separation of mononuclear cells and red blood cells from whole blood;
   an irradiation device adapted to receive the treatment container, and to subject the treatment container to a selected fixed emitted light dose; and
   a controller configured to control the separation device so that the suspension of mononuclear cells and red blood cells received in the treatment container has a predetermined hematocrit of 2.5% prior to irradiation and to control the irradiation device to deliver the selected fixed emitted light dose regardless of the hematocrit of the suspension of mononuclear cells and red blood cells;
   wherein the selected fixed emitted light dose is programmed into the controller, having previously been determined by generating a light attenuation curve relating hematocrit of the suspension of mononuclear cells and red blood cells to percent light absorbed by the red blood cells for a predetermined thickness of the treatment container when a known volume of the suspension of mononuclear cells and red blood cells is received therein, and targeting the selected fixed emitted light dose to a flat portion of the light attenuation curve.

* * * * *